United States Patent
Mentak

(10) Patent No.: US 6,852,820 B2
(45) Date of Patent: Feb. 8, 2005

(54) METHOD FOR PREPARING ACRYLIC COPOLYMER MATERIALS SUITABLE FOR OPHTHALMIC DEVICES

(75) Inventor: Khalid Mentak, Goleta, CA (US)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 10/115,133

(22) Filed: Apr. 4, 2002

(65) Prior Publication Data

US 2002/0151667 A1 Oct. 17, 2002

Related U.S. Application Data

(63) Continuation of application No. 09/265,527, filed on Mar. 9, 1999, now abandoned.

(51) Int. Cl.⁷ .............................................. C08F 220/46
(52) U.S. Cl. ................ 526/317.1; 526/307.6; 526/328.5; 526/347; 526/318.1; 526/318.44; 526/325; 526/326; 264/2.6; 623/6.11
(58) Field of Search .......................... 526/317.1, 307.6, 526/328.5, 325, 347, 318.1, 328, 318.44, 264, 303.1; 264/2.6; 623/6.11

(56) References Cited

U.S. PATENT DOCUMENTS

| | | | |
|---|---|---|---|
| 3,850,892 A | | 11/1974 | Shen et al. |
| 3,880,818 A | | 4/1975 | Shen et al. |
| 4,573,998 A | | 3/1986 | Mazzocco |
| 4,668,446 A | * | 5/1987 | Kaplan et al. ............... 264/1.7 |
| 4,834,750 A | | 5/1989 | Gupta |
| 5,194,544 A | | 3/1993 | Goldberg et al. |
| 5,217,491 A | * | 6/1993 | Vanderbilt ................ 623/6.46 |
| 5,290,892 A | * | 3/1994 | Namdaran et al. .......... 526/259 |
| 5,326,506 A | | 7/1994 | Vanderbilt |
| 5,331,073 A | * | 7/1994 | Weinschenk et al. ........ 526/264 |
| 5,359,021 A | | 10/1994 | Weinschenk, III et al. |
| 5,403,901 A | | 4/1995 | Namdaran et al. |
| 5,433,746 A | | 7/1995 | Namdaran et al. |
| 5,470,932 A | | 11/1995 | Jinkerson |
| 5,662,707 A | | 9/1997 | Jinkerson |
| 5,674,960 A | | 10/1997 | Namdaran et al. |
| 5,693,095 A | * | 12/1997 | Freeman et al. ........... 623/6.56 |

FOREIGN PATENT DOCUMENTS

| | | |
|---|---|---|
| EP | 0448978 | 10/1991 |
| EP | 0485197 | 5/1992 |
| JP | A-5-269191 | * 10/1993 |
| WO | WO 82/00147 | 1/1982 |
| WO | WO 96/40303 | 12/1996 |

* cited by examiner

*Primary Examiner*—Tatyana Zalukaeva
(74) *Attorney, Agent, or Firm*—Pillsbury Winthrop LLP

(57) ABSTRACT

Solid rigid acrylic copolymer materials, useful for forming ophthalmic devices, are processed into the shape of an ophthalmic device, such as an intraocular lens and are then processed into a foldable form. The acrylic copolymer material has polymer units derived from an $\alpha,\beta$-ethylenically unsaturated carboxylic acid monomer, such as, (meth)acrylic acid, 1-butenoic acid, and the like, and an aryl(meth)acrylate monomer, such as, phenyl(meth)acrylate, 2-ethyloxy(meth)acrylate, and the like. The processing into a foldable shape may be accomplished by contacting the rigid material, having a Tg of 25° C. or higher, with an alcohol, preferably in the presence of acid catalyst, to lower the Tg to 20° C. or less.

19 Claims, No Drawings

METHOD FOR PREPARING ACRYLIC COPOLYMER MATERIALS SUITABLE FOR OPHTHALMIC DEVICES

CROSS REFERENCE TO RELATED APPLICATIONS

This application is a continuation of application Ser. No. 09/265,527, filed Mar. 9, 1999 now abandoned, the entire disclosure of which is incorporated herein by reference thereto.

FIELD OF THE INVENTION

This invention relates to methods for converting rigid acrylic copolymer materials which are useful as ophthalmic devices, such as contact lenses, keratoprostheses, and corneal rings or inlays, into foldable form and to the resulting ophthalmic devices and such copolymer materials for making same. In particular, this invention relates to intraocular foldable lenses formed from acrylic copolymer materials, and the method for preparing such intraocular foldable lenses.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

The refractive power of a lens is a function of its shape and the refractive index of the material of which it is made. A lens made from a material having a higher refractive index can be thinner and provide the same refractive power as a lens made from a material having a relatively lower refractive index.

In general hydrogel materials have a relatively low refractive index, making them less desirable than other materials because of the thicker lens optic necessary to achieve a given refractive power. Silicone materials generally have a higher refractive index than hydrogels, but tend to unfold explosively after being placed in the eye in a folded position. Explosive unfolding can potentially damage the corneal endothelium and/or rupture the natural lens capsule of the eye. Acrylic materials are desirable because they typically have a high refractive index and unfold more slowly or controllably than silicone materials.

U.S. Pat. No. 5,290,892 (Namdaran et al.), U.S. Pat. No. 5,331,073, (Weinschenk, III et al.), and U.S. Pat. No. 5,693,095 (Freeman et al.), the complete disclosures of which are hereby incorporated by reference, discuss forming foldable lenses out of a polymer material derived from an ethoxyaryl (meth)acrylate with a crosslinker or with a second acrylate monomer and a crosslinker. Since the polymer material is soft/foldable, these patents discuss mold forming the polymer material to individually form the lens which requires specialized equipment and expensive customized molds. In addition, the resulting molded lenses have poor surface quality since they cannot be polished. Alternatively, there is discussion in U.S. Pat. No. 5,331,073 of forming lenses from a soft/foldable material by machining it at cryogenic temperatures.

U.S. Pat. No. 4,668,446 (Kaplan et al.), the complete disclosure of which is hereby incorporated by reference, alleviates the problems of mold forming the lenses and the process difficulties and expense associated with cryogenic machining of soft polymer materials by employing a process of forming a rigid polymer sheet that can be machined into lenses which are then esterified to render them foldable. The problem with this process is the polymers used to form the rigid polymer material have an inferior refractive index and it is essential in the esterification step to employ substantial processing equipment to remove water, including water formed by the esterification reaction. If virtually all the water is not removed, the resulting lenses tend to crumble or suffer from other mechanical infirmities. Moreover, these lenses tend to become opaque in aqueous environments.

SUMMARY OF THE INVENTION

The present invention relates to an acrylic copolymer material, useful for forming ophthalmic devices, comprising polymer units derived from an $\alpha,\beta$-ethylenically unsaturated carboxylic acid monomer and a (meth)acrylate monomer having at least one aromatic group (herein referred to as an "aryl(meth)acrylate"). The invention also provides a process for making ophthalmic devices such as lenses, in particular intraocular lenses. The process comprises: (a) forming a rigid copolymer, for instance in the form of a sheet suitable for preparing the desired ophthalmic device, by copolymerizing at least one $\alpha,\beta$-ethylenically unsaturated is caboxylic acid and at least one aryl(meth)acrylate, (b) forming an ophthalmic device from the copolymer sheet, and (c) processing the ophthalmic device to render it foldable.

DESCRIPTION OF THE PREFERRED EMBODIMENTS

Herein certain terms are used to define certain chemical elements, groups and compounds. Unless otherwise qualified, these terms are to be understood as having the meanings as defined below.

"alkylene" refers to a saturated divalent hydrocarbyl group.

"copolymer" refers to a polymer compound having at least two different polymer units.

"(meth)acrylate" refers to acrylate, methacrylate, or a mixture thereof.

"hydrocarbyl" refers to a radical group containing only carbon and hydrogen. If not otherwise stated, hydrocarbyl as used herein preferably refers to a univalent radical group containing 1 to about 30 carbon atoms.

"substituted hydrocarbyl" refers to a hydrocarbyl radical that contains one or more substituent groups.

"unsubstituted hydrocarbyl" refers to a hydrocarbyl radical that contains no substituent groups.

The present invention provides an acrylic copolymer material for forming ophthalmic devices. Preferably, the ophthalmic devices include intraocular lenses.

The acrylic copolymer material of the present invention comprises polymer units derived from the polymerization of at least one $\alpha,\beta$-ethylenically unsaturated is carboxylic acid monomer with at least one aryl(meth)acrylate monomer, and a crosslinking agent.

Suitable α,β-ethylenically unsaturated carboxylic acid monomers include monomers represented by formula (I)

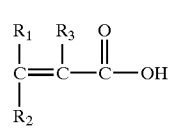

wherein $R_1$ and $R_2$ independently represent a hydrogen atom or an allyl group having up to 6 carbon atoms and $R_3$ represents a hydrogen atom or a methyl group. Specific representative examples of suitable carboxylic acid monomers include acrylic acid, methacrylic acid, 1-butenoic acid, isopentene-2-oic acid, 2,3-dimethylbutene-2-oic acid, 2-methylpentene-2-oic acid, tiglic acid, angelic acid, senecioic acid, maleic acid, itaconic acid, and the like. Of these, acrylic acid is preferred.

Suitable aryl(meth)acrylate monomers include monomers represented by the formula (II):

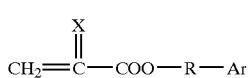

wherein:

X represents a hydrogen atom or a methyl group; and

R represents a covalent bond, or a substituted or unsubstituted hydrocarbyl group.

Ar is any aromatic ring, such as benzene, which can be unsubstituted or substituted with H, $CH_3$, $C_2H_5$, n-$C_3H_7$, iso-$C_3H_7$, $OCH_3$, $C_6H_{11}$, Cl, Br, $C_6H_5$ or $CH_2C_6H_5$.

In a preferred form of formula (II), R represents unsubstituted and substituted, including halo- substituted, alkyl, alkylaryl, alkoxy, aryl, aryloxy, arylalkoxy, alkylarylalkyl, alkylaryloxy and alkylarylalkoxy, more preferably an alkoxy and aryloxy, most preferably a 1–6 carbon alkoxy.

Suitable aryl(meth)acrylate monomers include, for example: phenyl methacrylate, 2-ethylphenoxy methacrylate, 2-ethylphenoxy acrylate, hexylphenoxy methacrylate, hexylphenoxy acrylate, benzyl methacrylate, 2-phenylethyl methacrylate, 4-methylphenyl methacrylate, 4-methylbenzyl methacrylate, 2-2-methyphenylethyl methacrylate, 2-3-methylphenylethyl methacrylate, 2-4-methylphenylethyl methacrylate, 2-4-propylphenyl)ethyl methacrylate, 2-(4-(1-methylethyl)phenyl)ethyl methacrylate, 2-(4-methoxyphenyl)ethytmethacrylate, 2-(4-cyclohexylphenyl)ethyl methacrylate, 2-(2-chlorophenyl) ethyl methacrylate, 2-(3-chlorophenyl)ethyl methacrylate, 2-(4-chlorophenyl)ethyl methacrylate, 2-(4-bromophenyl) ethyl methacrylate, 2-(3-phenylphenyl)ethyl methacrylate, 2-(4-phenylphenyl)ethyl methacrylate), 2-(4-benzylphenyl) ethyl methacrylate, and the like, including the corresponding methacrylates and acrylates.

The copolymerizable cross-linking agent useful in forming the copolymeric material of this invention includes any terminally ethylenically unsaturated compound having more than one unsaturated group. Preferably, the cross-linking agent includes compounds having at least two (meth) acrylate and/or vinyl groups. Particularly preferred cross-linking agents include diacrylate compounds represented by the following formula (III):

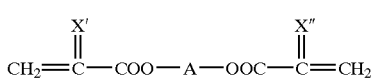

wherein

X' and X" independently represent a hydrogen atom or a methyl group; and

A represents a substituted or unsubstituted divalent hydrocarbyl group. In a preferred form of formula (III), A represents a substituted or unsubstituted divalent aliphatic radical, and preferably a 1–6 carbon alkylene.

Suitable cross-linking agents include, for example: diacrylate compounds including ethylene glycol dimethacrylate, diethylene glycol dimethacrylate, polyethylene glycol dimethacrylate, allyl methacrylate, 1,3-propanedioldimethacrylate, allylmethacrylate 1,6-hexanediol dimethacrylate, 1,3-butanediol dimethacrylate, 1,4-butanediol dimethacrylate as well as divinyl compounds including divinyl hydrocarbons and divinyl benzene, and the like.

The proportions of the monomers should preferably be chosen to produce a polymer having a glass transition temperature of at least 25° C., preferably at least 30° C. and more preferably at least 35° C. Preferably, the acrylic copolymer material is derived from components comprising, relative to the total weight of monomer components:

5–70 wt. %, preferably 5–50 wt. %, of at least one α,β-ethylenically unsaturated carboxylic acid monomer; and 10–95 wt. %, preferably 35–70 wt. %, of at least one aryl(meth)acrylate monomer.

The crosslinking agent may be introduced in an amount, relative to the total weight of monomer components, of between 0.5 and 15 wt. %, preferably 1–10 wt. %. In addition, a free radical inhibitor may be introduced in an amount of between 0.5 to 2 wt. %.

Preferably, the acrylic copolymer material of the present invention includes those having a water absorption value of less than 0.5%.

In addition to the carboxylic acid monomer and the aryl(meth)acrylate monomer, the acrylic copolymer material may also include polymer units derived from other monomers such as, for example, esters and anhydrides of α,β-ethylenically unsaturated carboxylic acids. Suitable esters include the alky, hydroxyalkyl and alkoxyalkyl esters of the α,β-ethylenically unsaturated carboxylic acids in which the alkyl, hydroxyalklyl or alkoxyalkyl substituent may have up to about 11 carbon atoms. Such esters include those represented by the following formula (IV):

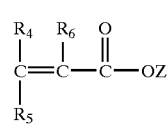

wherein $R_4$ and $R_5$ independently represent a hydrogen atom or an alkyl group having up to 6 carbon atoms, $R_6$ represents a hydrogen atom or a methyl group and Z is an alkyl, hydroxyalkyl, or alkoxyalkyl group having up to about 11 carbon atoms. Specific representative examples of suitable esters include the methyl, ethyl, n-propyl, i-propyl, and butyl acrylates and methacrylates; 2-hydroxyethyl acrylate and methacrylate, 2-hydroxypropyl acrylate and methacrylate, and the like.

One or more of these additional monomers may be used in the formation of the acrylic copolymer material of the present invention. These additional monomers are preferably used in an amount, relative to the total weight of monomers, of between 3–40 wt. %, more preferably, in an amount of between 5–30 wt. %.

If desired, the formation of the acrylic copolymer may include additional additives conventional in the art. For example, mold release compounds or processing additives such as lecithin may be added which may or may not remain in the polymer following dehydration. Other additives which may be desired to remain in the esterified polymer, such as UV absorbers or dyes, should be properly selected so that they are not removed or chemically altered during dehydration of the polymer and any subsequent processing. Such additives may, for example, be covalently bonded to the polymer so that they are not removed. Suitable UV absorbers include vinyl benzophenone, vinyl benzotriazole, vinyl phenothiazine, and the like. Suitable free radical initiators include 2,2'-azobisisobutyronitrile(AIBN), benzoyl peroxide, acetyl peroxide, lauryl peroxide, t-butyl peroxide, and the like.

The copolymer material of the present invention may be formed by any polymerization technique suitable for this purpose. For instance, the carboxylic acid and the aryl(meth) acrylate monomer may be mixed along with any additional monomers or additives and exposed to conditions and/or catalyst suitable to polymerize the mixture. The monomer mixture may be polymerized by a catalyst such as a peroxide, actinic light, and/or by the use of heat and/or pressure.

Preferably, the acrylic copolymer material is formed in the shape of a sheet suitable for forming ophthalmic devices, such as intraocular lenses. The ophthalmic devices of the desired dimension, and if applicable diopter, are cut from the rigid copolymer sheet using conventional lathe cutting techniques at room temperature. The lenses may be, and preferably are, polished by conventional techniques (including tumble polishing).

The ophthalmic devices formed are then processed to transform the acrylic copolymer material from a rigid material to a material that is foldable. The processing of the rigid acrylic copolymer material to render the material foldable is preferably effected by placing the devices formed from the hard material in a liquid alcohol at an elevated temperature, preferably from about 60° C. to about 140° C., optionally in the presence of a catalyst, such as a soluble acid, preferably sulfuric acid, in a concentration of from about 0.2 to about 5 percent by weight of the alcohol. The resulting ophthalmic device material will preferably have a glass transition temperature of 20° C. or less. After such processing, it is preferred that the resulting ophthalmic device material has a refractive index of greater than 1.50.

It is preferred that the processing be achieved by the use of an alcohol containing up to 15 carbon atoms. Preferably the alcohol used will have from 3 to 7 carbon atoms. Alcohols having fewer than 3 carbon atoms are less effective in softening the device material while alcohols having more than 7 carbon atoms take progressively longer to diffuse into the interior of the copolymeric material. The processing may include esterification and/or dehydration of the acrylic copolymer material.

After the device material is rendered foldable, the device is removed from the alcohol. Unreacted alcohol is removed from the device material. This may be achieved by drying alone or a combination of drying and rinsing with an alcohol having 3 carbons or less, preferably propanol. Drying may be accomplished by exposing the device to a temperature of about 20–25° C. for ten to twelve hours depending on the humidity of the environment and the particulars of the device.

Alternatively or additionally, the device may dried in a vacuum oven or other suitable equipment at an elevated temperature, generally up to about 120° C. The time and steps required to substantially remove the residual alcohol from the device will depend on the particular alcohol, the type of polymer, dimensions of the device, and the drying conditions. At 95° C., for example, removal of the alcohol is substantially complete after about 12 hours in a vacuum oven.

In another aspect, the invention provides a novel method of attaching a haptic to the ophthalmic device, in particular, attaching a haptic to the lens without damaging the lens. Broadly, the method includes the steps of (a) forming a peripheral bore in the lens; (b) swelling the lens with an organic fluid; (c) inserting an end of a haptic into the peripheral bore of the swollen lens, the end having an enlarged transverse cross-sectional portion; and (d) removing the organic fluid from the lens to cause the lens to contract, whereby the haptic is secured to the lens by contraction of the peripheral bore about the enlarged portion of the end of the haptic.

EXAMPLES

The following examples are given as particular embodiments of the invention and to demonstrate the practice and advantages thereof. It is understood that the examples are given by way of illustration and are not intended to limit the specification or the claims that follow in any manner.

Examples 1–7

Rigid copolymer sheets were cast from proportions of polymer material as set forth in the table below, along with 0.3% of a UV absorber. The UV absorber used is vinyl functionalized benzotriazole with the trade name of Norbloc™. Lenses of the desired diopter and dimensions were lathe cut from the hard polymer sheets and then tumble polished. The finished lenses were soaked in alcohol containing sulfuric acid. The lenses were removed, washed with propanol, and dried. All samples had good foldability and optical properties.

TABLE 1

| Example | Formulation | Reaction Time (Hr) | Reaction Medium | | Temp (° C.) |
|---|---|---|---|---|---|
| | | | Alcohol | Catalyst | |
| 1 | 55% EGPEA 26% MMA 14% AA 5% EGDM | 336 | n-propanol | 5% $H_2SO_4$ | 90° C. |
| 2 | 56% EGPEA 31% MMA 10% AA 3% BDA | 18 | hexyl alcohol | 2% $H_2SO_4$ | 123° C. |
| 3 | 63% EGPEA 31% AA 6% EGDM | 48 | Propanol | $H_2SO_4$ | 100° C. |

TABLE 1-continued

| Example | Formulation | Reaction Time (Hr) | Reaction Medium | | |
|---|---|---|---|---|---|
| | | | Alcohol | Catalyst | Temp (° C.) |
| 4 | 61% EGPEA<br>14% AA<br>15% MMA<br>10% EGDM | 60 | Propanol | $H_2SO_4$ | 100° C. |
| 5 | 54% EGPEA<br>7% EMA<br>29% AA<br>10% EGDM | 48 | Propanol | $H_2SO_4$ | 100° C. |
| 6 | 60% EGPEMA<br>38% AA<br>2% EGDM | 240 | Propanol | $H_2SO_4$ | 100° C. |
| 7 | 50% EGPEMA<br>48% AA<br>2% EGDM | 24 | Propanol | $H_2SO_4$ | 100° C. |

Table Notes:
AA: Acrylic acid
BDDA: 1,3 butanediol diacrylate
EGDM: Ethylene glycol dimethacrylate
EGPEA: Ethylene glycol phenylethyl acrylate
EGPEMA: Ethylene glycol phenylethyl methacrylate
EMA: Ethyl methacrylate
MMA: Methyl methacrylate Example 8

The following monomers were mixed in a glass flask for 30 minutes using a stir bar:

| | |
|---|---|
| Ethylene glycol phenylethyl methacrylate | 82.50 g |
| Acrylic acid | 21.00 g |
| Methyl methacrylate | 39.01 g |
| Ethylene glycol dimethacrylate | 7.50 g |
| 2,2'-Azobisisobutyronitrile | 0.30 g |
| Norbloc* | 0.75 g |

Note:
*Norbloc is a UV absorber available from Ciba Geigy.

The resulting solution was degassed using Nitrogen, then injected between a mold comprised of two glass plates held with binder clips. A piece of tubing is used as a gasket material to adjust the thickness of the polymer sheet. The mold is placed in a water bath at 58° C. for 22 hours then in a vacuum oven at 96–98° C. for another 22 hours. The resulting material is a hard clear sheet of an acrylic polymer. The glass transition temperature was found to be 33.8° C. The refractive index was found to be 1.536.

Intraocular lenses were machined from the hard polymer sheet. The lenses had good dimensional stability and resolution. The lenses were then tumble polished at 85 r.p.m. for 3 days. The tumble polished lenses had excellent surface and edge quality. The lenses were then placed in a reflux apparatus containing 98% hexyl alcohol by weight and 2% sulfuric acid by weight for 18 hours. The temperature was kept at 120° C.±2° C. The lenses were then washed/extracted in a soxhlet apparatus using n-propanol for 24 hours. The finished lenses were dried at 98° C. for 24 hours. The lenses were foldable, had excellent optical resolution, and excellent surface quality. The glass transition temperature was found to be 3.3° C. The refractive index was found to be 1.5002.

Example 9

The following monomers were mixed as described in Example 8:

| | |
|---|---|
| Ethylene glycol phenylethyl methacrylate | 84.01 g |
| Acrylic acid | 15.00 g |
| Methyl methacrylate | 46.52 g |
| 1,3 Butanediol Dimethacrylate | 4.50 g |
| AlBN | 0.30 g |
| Norbloc | 0.75 g |

A hard polymer sheet was prepared as described in Example 8. The Tg was 30° C. and the refractive index was 1.5323. Foldable lenses were prepared as described is in Example 8. The Tg of the foldable material was 3° C. and the refractive index was 1.5001. The water absorption was determined to be 0.1%.

Having described specific embodiments of the present invention, it will be understood that many modifications thereof will readily appear or may be suggested to those skilled in the art, and it is intended therefore that this invention is limited only by the spirit and scope of the following claims.

What is claimed is:

1. A method for preparing a foldable ophthalmic material suitable for use as an intraocular device, said method comprising, shaping a solid rigid material formed from an acrylic copolymer material having a glass transition temperature, Tg, of at least 25° C. and comprising polymer units derived from:
an α,β-ethylenically unsaturated carboxylic acid monomer, and
an aryl(meth)acrylate monomer, wherein said shape is suitable as an ophthalmic device, and
contacting the solid rigid material with alcohol to lower its glass transition temperature to thereby render the solid rigid material foldable.

2. The method according to claim 1, wherein said shaping is carried out at room temperature.

3. The method according to claim 1, wherein said acrylic copolymer has a Tg of at least 30° C.

4. The method according to claim 1, wherein said solid material has a refractive index of greater than 1.50.

5. The method according to claim 1, wherein said solid material has a water absorption value of less than 0.5%.

6. The method according to claim 1, wherein said α,β-ethylenically unsaturated carboxylic acid monomer includes monomers represented by formula (I):

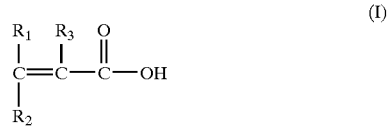

(I)

wherein $R_1$ and $R_2$ independently represent a hydrogen atom or an alkyl group having up to 6 carbon atoms, and $R_3$ represents a hydrogen atom or a methyl group.

7. The method according to claim 1, wherein said aryl (meth)acrylate monomer includes monomers represented by formula (II):

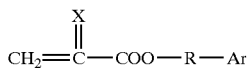 (II)

wherein:

X represents a hydrogen atom or a methyl group;

R represents a covalent bond, or a substituted or unsubstituted hydrocarbyl group; and Ar is an aromatic ring, which can be unsubstituted or substituted with $CH_3$, $C_2H_5$, $n$-$C_3H_7$, $iso$-$C_3H_7$, $OCH_3$, $C_6H_{11}$, Cl, Br, $C_6H_5$ or $CH_2C_6H_5$.

8. The method according to claim 1, wherein said material further comprises crosslink units derived from a diacrylate compound.

9. The method according to claim 8, wherein said diacrylate compound includes compounds represented by formula (III):

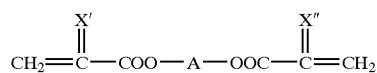 (III)

wherein

X' and X" independently represent a hydrogen atom or a methyl group; and

A represents a substituted or unsubstituted divalent hydrocarbyl group.

10. The method according to claim 1, wherein said material further comprises polymer units derived from monomers represented by the following formula (IV):

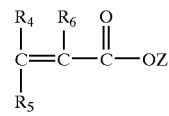 (IV)

wherein $R_4$ and $R_5$ independently represent a hydrogen atom or an alkyl group having up to 6 carbon atoms, $R_6$ represents a hydrogen atom or a methyl group, and Z is an alkyl, hydroxyalkyl, or alkoxyalkyl group having up to about 11 carbon atoms.

11. The method according to claim 1, wherein the glass transition temperature is lowered to 20° C. or less.

12. The method according to claim 1, wherein the solid rigid material is immersed in liquid alcohol at a temperature in the range of from about 60° C. to about 140° C.

13. The method according to claim 12, wherein the liquid alcohol further comprises a soluble acid catalyst.

14. The method according to claim 1, wherein the foldable ophthalmic material has a refractive index greater than 1.5.

15. The method according to claim 1, wherein said alcohol has from 3 to 7 carbon atoms.

16. The method according to claim 1, wherein the solid rigid material before shaping has the shape of a sheet and wherein said shaping step comprises shaping said sheet into an intraocular lens.

17. The method according to claim 1, wherein the solid rigid material before shaping has the shape of a sheet and wherein said shaping step comprises shaping said sheet into an intraocular lens.

18. An ophthalmic device formed by the method of claim 1.

19. The ophthalmic device according to claim 18, wherein said ophthalmic device is an intraocular lens.

* * * * *